United States Patent [19]

Sugarbaker

[11] Patent Number: 5,403,343
[45] Date of Patent: Apr. 4, 1995

[54] EXPANDING POLYGONAL SURGICAL COMPRESSOR

[75] Inventor: David J. Sugarbaker, Brookline, Mass.

[73] Assignee: Brigham & Women's Hospital, Boston, Mass.

[21] Appl. No.: 255,113

[22] Filed: Jun. 7, 1994

Related U.S. Application Data

[63] Continuation of Ser. No. 929,340, Aug. 13, 1992, abandoned.

[51] Int. Cl.⁶ .............................................. B61B 17/28
[52] U.S. Cl. ...................................... 606/207; 606/151
[58] Field of Search ............... 606/205, 206, 207, 208, 606/151, 106, 122, 198; 604/105; 81/418, 419, 420; 128/17

[56] References Cited

U.S. PATENT DOCUMENTS

| | | | |
|---|---|---|---|
| 1,433,031 | 10/1922 | Pegaitaz | 606/198 |
| 2,655,154 | 11/1951 | Richter | |
| 3,667,474 | 6/1972 | Lapkin et al. | 606/198 |
| 3,857,395 | 12/1974 | Johnson et al. | 606/198 X |
| 4,655,223 | 4/1987 | Kim | |
| 4,763,669 | 8/1988 | Jaeger | |
| 4,803,983 | 2/1989 | Siegel | |
| 5,152,279 | 10/1992 | Wilk | 128/17 |
| 5,178,133 | 1/1993 | Pena | 604/105 X |

FOREIGN PATENT DOCUMENTS 1424813  9/1988  U.S.S.R. ............................. 606/151

OTHER PUBLICATIONS

International Search Report.

Primary Examiner—Michael H. Thaler
Attorney, Agent, or Firm—Hamilton, Brook, Smith & Reynolds

[57] ABSTRACT

An expanding polygonal surgical compressor has a first planar frame with at least three articulated frame members extendable from a compressed configuration to an extended configuration forming a polygon. A second planar frame has frame members corresponding to the frame members of the first frame. The second frame is pivoted to the first frame for movement from an open to a closed or tissue compressing position.

11 Claims, 5 Drawing Sheets

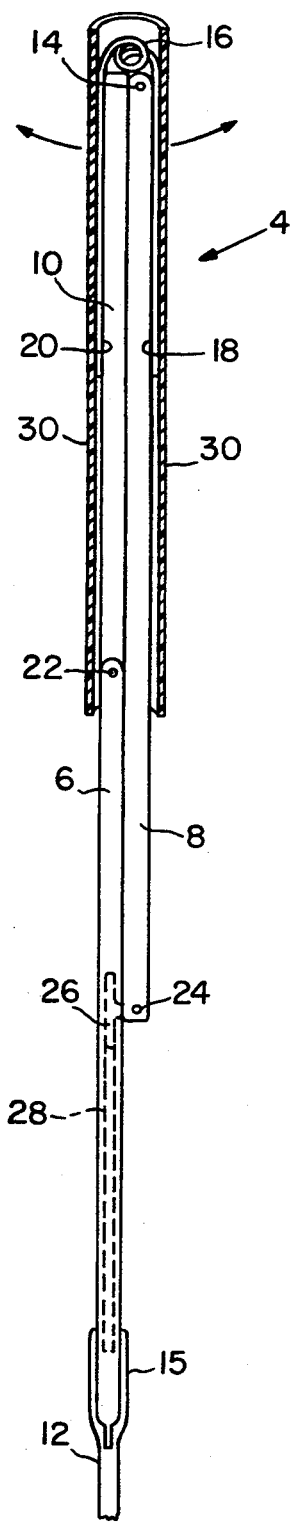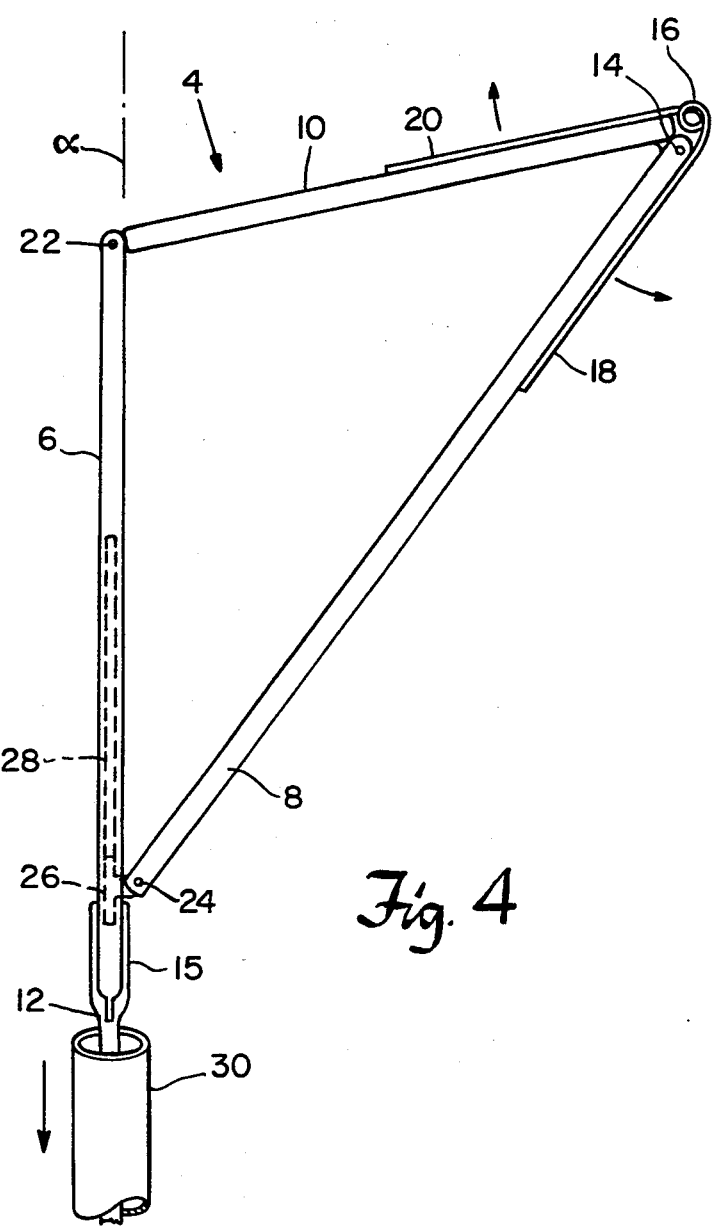
Fig. 3
Fig. 4

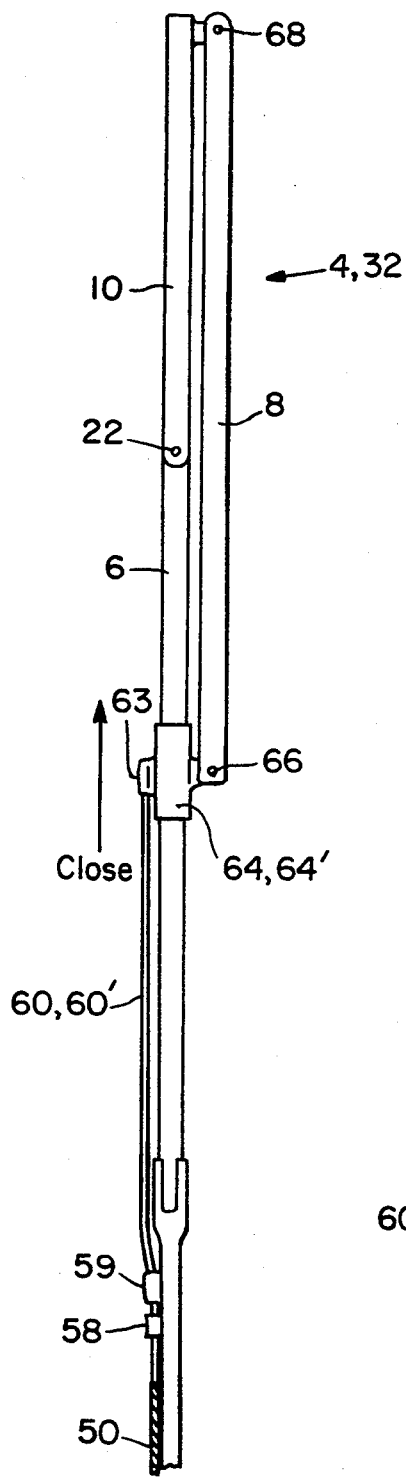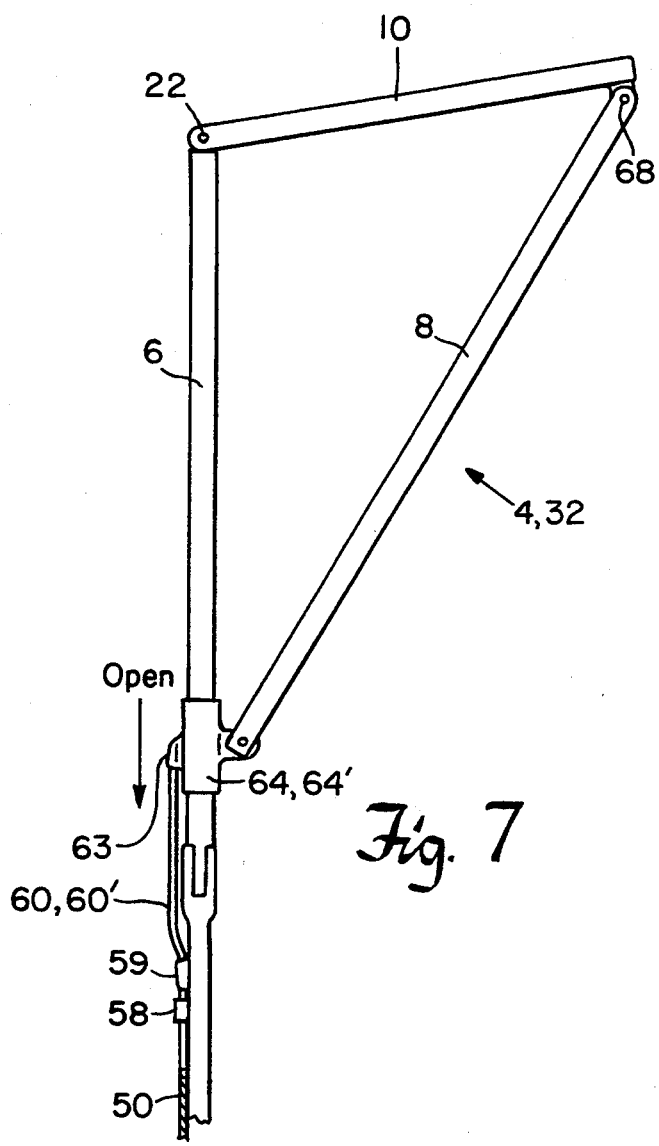
Fig. 6
Fig. 7

EXPANDING POLYGONAL SURGICAL COMPRESSOR

This application is a continuation of application Ser. No. 07/929,340, filed Aug. 13, 1992, now abandoned.

BACKGROUND OF THE INVENTION

Endoscopic or video surgery is a relatively new medical procedure. It involves a surgeon making a small incision in a patient and inserting a lens and light source connected by cables to a video camera which, in turn, is connected to a monitor.

The endoscope, i.e., lens and light source elements are combined in a rod-like structure which is inserted in an area such as, for example, the abdomen or the chest. One or more other incisions are also made, through which functioning surgical instruments are inserted with their handles or equivalent operating mechanisms remaining outside the patient. The surgeon performs his work interiorally through the small incisions while watching the entire procedure on the video monitor.

The benefits from endoscopic surgery are numerous. Large scars are eliminated, the process, in many instances, is relatively bloodless and is much less traumatic to the patient than open surgery. The patient can leave the hospital in a far shorter period than after open surgery. This has economic benefits as well as emotional.

As indicated above, endoscopic surgery is performed with surgical instruments inserted through very small incisions. One problem is that the instruments themselves must be narrow enough to be able to be inserted into a patient without causing undue trauma. The surgeon may employ liners or mechanical orifices generally less than an inch in diameter which, themselves, are placed in the incisions.

Another problem encountered in surgery, endoscopic or open, is the necessity for operating on parts of the body which are moving as, for example, the heart or the lungs. This is made even more complicated by the fact that both of these organs are in the chest cavity and the thoracic surgeon, by necessity, must enter the cavity through incisions generally made between the ribs. Thus arises the dual objective of this invention of providing instruments which are narrow enough to enter between the ribs and which are capable of manipulating moving organs such as the heart or the lungs. It is to these objectives that the present invention is directed.

SUMMARY OF THE INVENTION

The invention resides in an instrument for use in endoscopic surgery for compressing tissue or organs. The instrument comprises a first planar frame having at least three articulated frame members extendable from a compressed configuration wherein the members are parallel to each other to an extended configuration in the form of a polygon. There is a second planar frame having frame members corresponding to the frame members of the first frame. The second frame is pivoted relative the first frame for movement from a substantially open position wherein the frames are at an angle with each other in position for gripping tissue to a closed or tissue compressing position wherein the planes of the frames may approach parallelism.

When the members of each frame are in their closed or compressed configuration, they are essentially parallel to each other, and when in their extended configuration, they form a polygon with the same number of sides as the number of frame members.

There are manually operated means in the form of scissors-like gripping handles for moving the frames between the open and closed positions.

A tube or sleeve may be employed to urge both frames into their assembled positions for inserting the instrument into and removing it from an incision in a patient.

In one embodiment of the invention, the means for moving the frames between their compressed and their extended configurations are cable operated means which permit the formation of a polygons of varying sizes at the will of the surgeon.

In another embodiment of the invention, the frame members are automatically opened when the sleeve has been removed by spring means attached to at least two of the frame members.

The above and other features of the invention including various and novel details of construction and combination of parts will now be more particularly described with reference to the accompanying drawings and pointed out in the claims. It will be understood that the particular expanding polygonal surgical compressor instrument embodying the invention is shown by way of illustration only and not as a limitation of the invention. The principles and features of this invention may be employed in varied and numerous embodiments without departing from the scope of the invention.

BRIEF DESCRIPTION OF THE DRAWINGS

FIG. 3 is a view of one of the frames of the compressor in its compressed configuration.

FIG. 4 is a side view of the frames of FIG. 3 in its extended configuration.

FIG. 6 is a side view of one of the frames of the embodiment of FIG. 5 in its compressed configuration.

FIG. 7 is a view of the frames of FIG. 6 in open extended configuration.

DETAILED DESCRIPTION OF THE INVENTION

Figure 1:
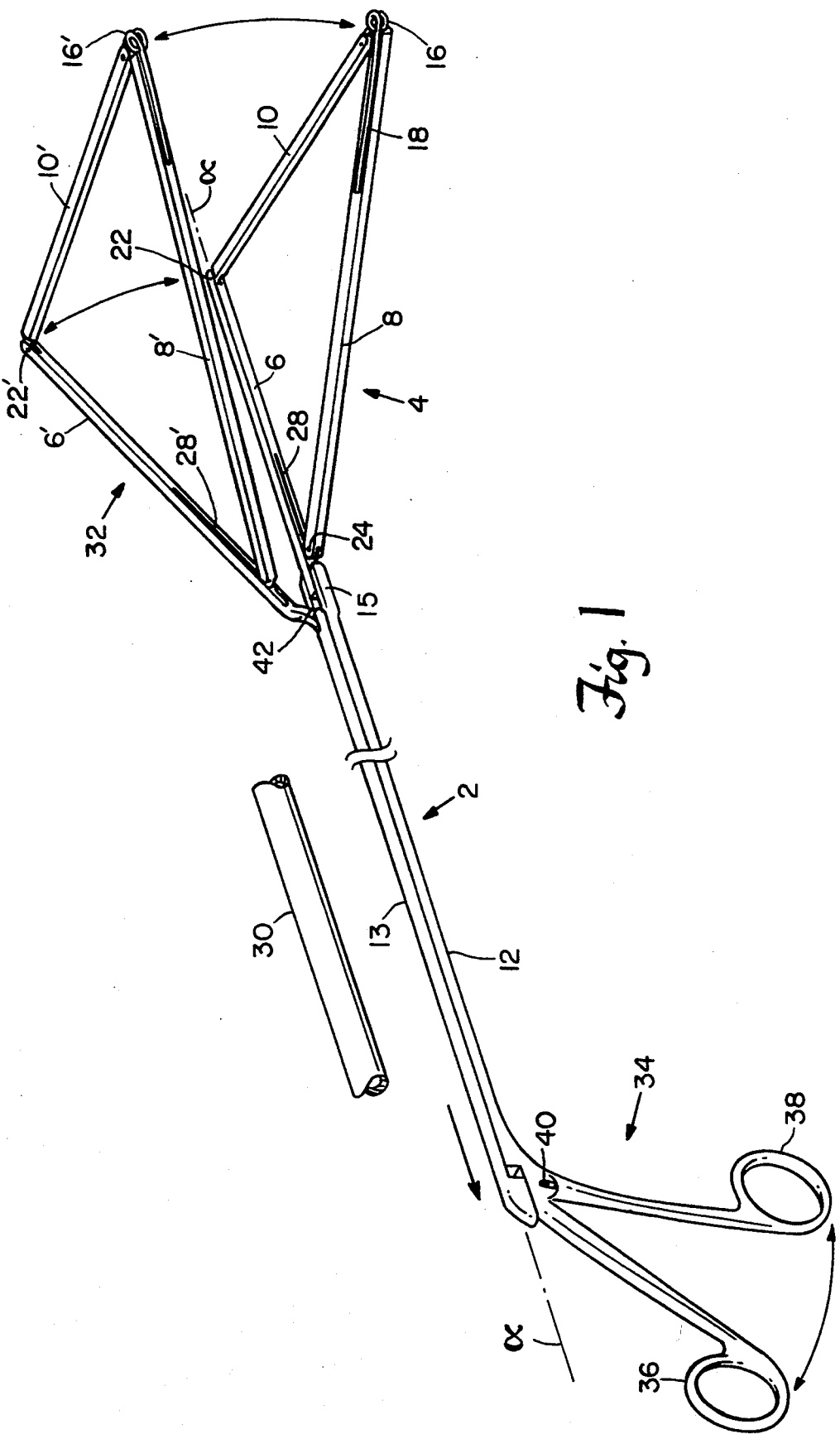
FIG. 1 is a perspective view of an expanding, polygonal surgical compressor for use in endoscopic surgery.

Referring first to FIG. 1, the invention is embodied in a surgical compressor having a substantially straight body 2 formed along an axis $\alpha$. A first polygonal frame, generally designated 4, has at least three articulated frame members 6, 8, and 10. It will be understood that whereas the invention is illustrated in a polygon having three frame members describing a triangle, four or more frame members could be employed without departing from the scope of the invention. The more frame members there are, the more the polygon approaches circular configuration.

The first frame member 6 is oriented along an extension of the axis $\alpha$ of the body 2. It is rigidly attached to a lower, relatively immovable body member 12, by means of a clevis-like member 15. The remaining frame members 8 and 10 are angularly extendable from a compressed configuration as seen in FIG. 3. In this configuration, the remaining members 8 and 10 are substantially in engagement with and parallel to the first frame member 6.

The frame members 8 and 10 are movable to an extended configuration shown in FIG. 4 wherein they form a three sided polygon. Frame member 8 is pivoted at 14 on the frame member 10. A coil spring 16 having arms 18 and 20 secured to the frame members 8 and 10, respectively, tend to urge the frame members apart. That is, from the FIG. 3 to the FIG. 4 position.

The frame member 10 is pivoted at 22 on the first frame member 6. A rider 26 which slides in a groove 28 in the frame member 6 is pivoted at 24 on the lower end of the frame member 8.

In the compressed configuration shown in FIG. 3, the rider 26 is at the upper end of the groove 28 and in the extended configuration shown in FIG. 4, it is at the lower end of the groove 28 under the force of the coil spring 16.

To maintain the frame 4 in the compressed configuration as shown in FIG. 3, a circular tube 30 is positioned over the frame member 4 and a second corresponding frame member hereinafter to be described.

A second polygonal frame 32 has frame members corresponding to those of the first frame 4. The parts of the second frame 32 corresponding to those of the first frame 4 and are designated by figures indicated as prime.

In a manner common to many surgical instruments, the movable body member 13 slides on the relatively immovable body member 12 and is operated by a hinged scissors grip generally designated 34. The scissors have a rigid grip member 36 and a movable member 38 pivoted at 40 on the frame member 12 which is an integral extension of the grip member 36.

Figure 2:
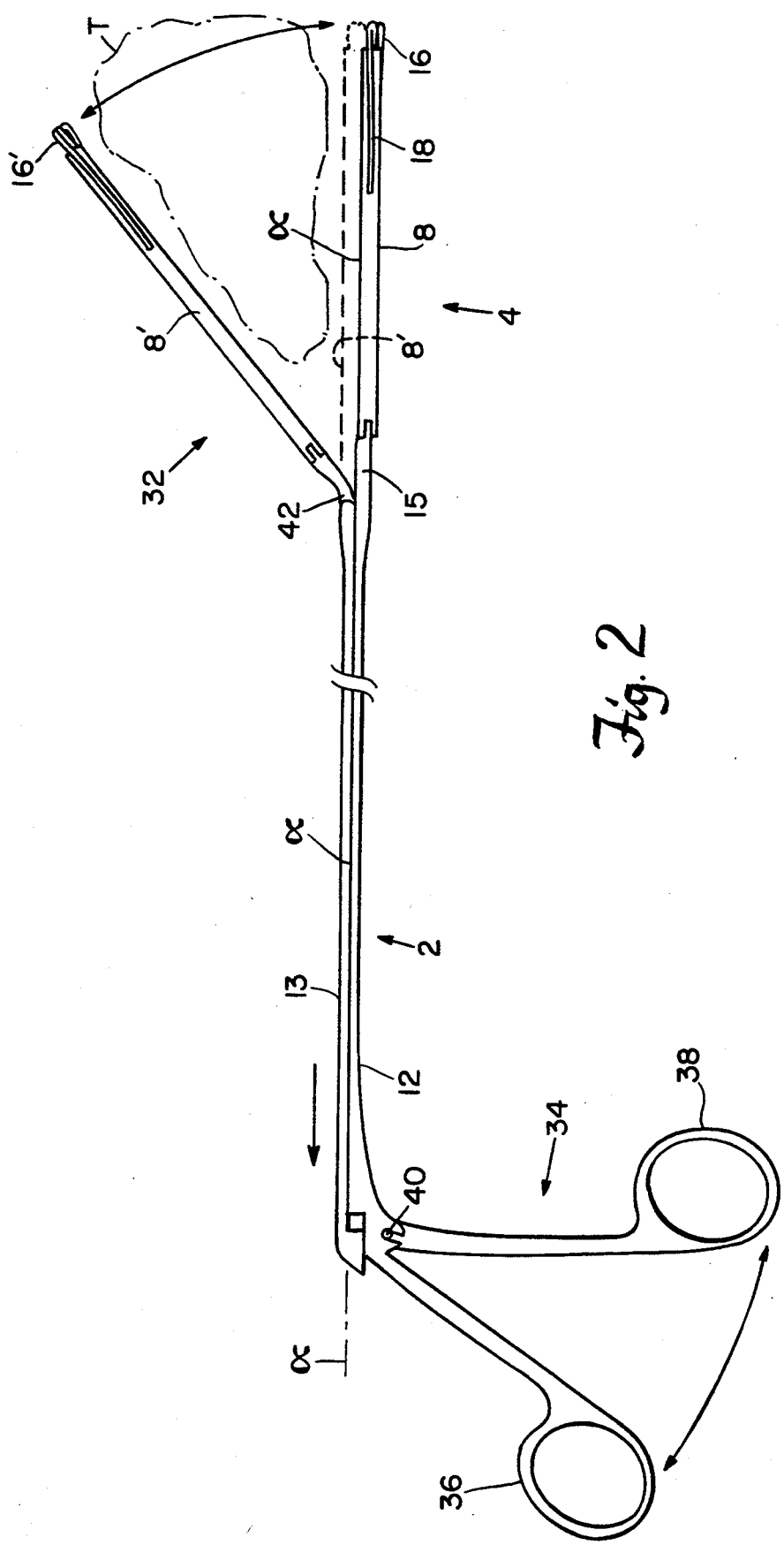
FIG. 2 is a side view of the compressor shown in FIG. 1.

The second polygonal frame 32 is linked to the movable member 13 at 42 to permit opening and closing of the frames 4 and 32. When open, the frames are oriented at an angle with each other for gripping tissue as seen in FIG. 2. They can move to the closed dotted line position with the second frame member 32 substantially superposed on the first frame member 4. Obviously, they will not completely close when they are gripping tissue or an organ. The tissue T lying within the confines of the polygonal frame members may then be cut, stitched, stapled, sutured and the like. In this position, the tissue is held relatively stationary as compared with its normal moving or pulsating condition were it a heart or a lung.

Referring to FIG. 3, the tube or sheath 30 urges both frames 4 and 32 into their compressed configuration for inserting the instrument into and removing it from an incision in a patient. In the insertion process, the tube or sheath 30 would occupy essentially the position shown in FIG. 3. After the frames have been inserted through the incision into the body cavity, the sheath 30 is slid downwardly as viewed in FIG. 3 or toward the scissors-like portion until it occupies a position surrounding the body 2 while the operation is performed.

To remove the instrument, the frames 4 and 32 are moved by the scissors to their closed positions and the tube advanced upwardly from the FIG. 4 to the FIG. 3 position for removal.

Figure 5:
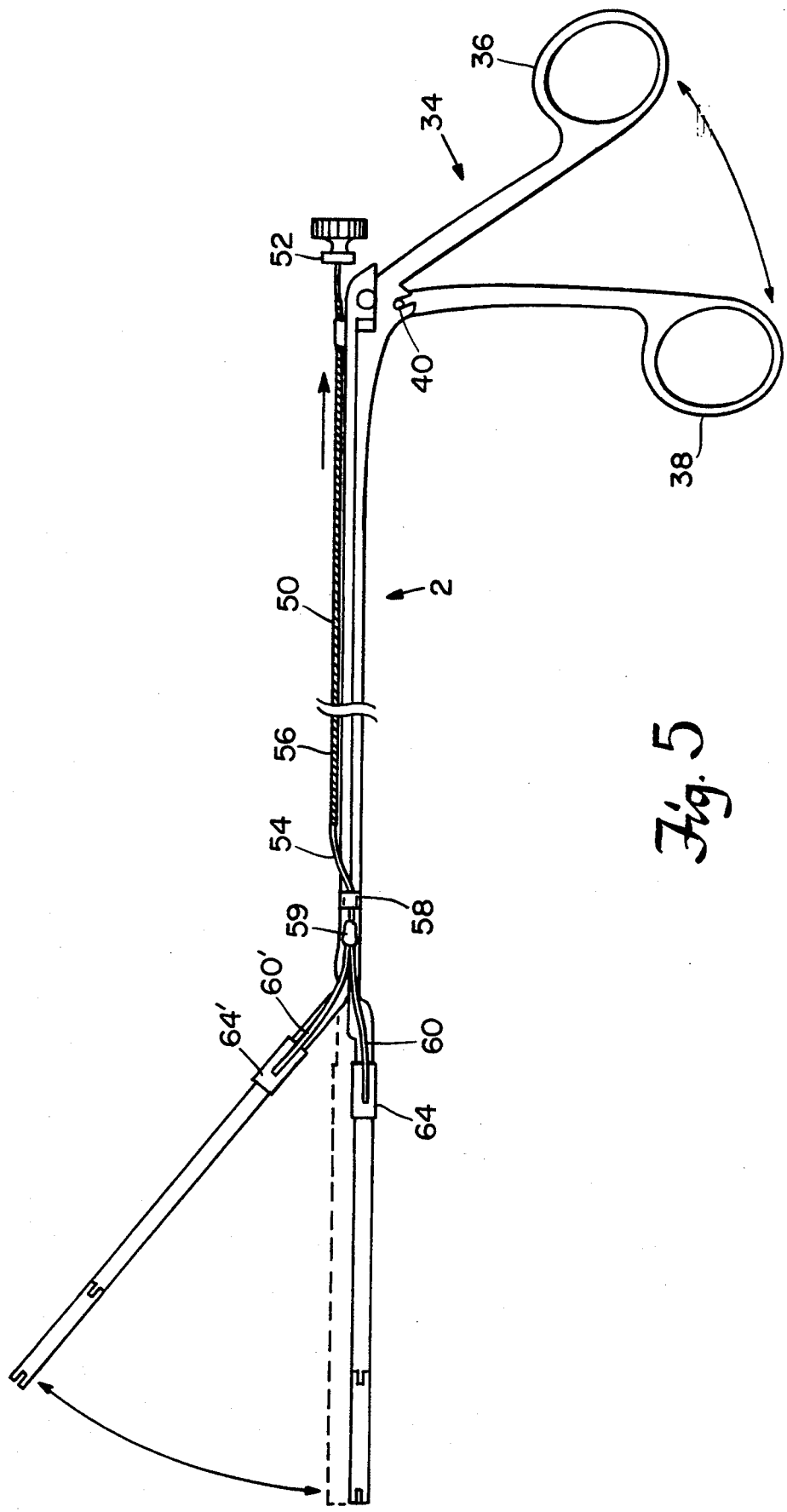
FIG. 5 is side view of another embodiment of the compressor made in accordance with the present invention.

FIGS. 5, 6 and 7 illustrate an alternative embodiment of the invention wherein the spring 16 for extending or opening the frame is replaced by a manually operated means on the body for moving the second frame 32 to the closed position relative to the frame 4 to the open position. It employs a sheathed cable 50 having a finger grip 52. The cable core 54 extends outwardly of the sheath 56 through a guide 58 and is secured at 59 to individual cables 60 and 62. Each cable is attached at 63 to a circular slider 64, 64' as seen in FIGS. 6 and 7.

After the instrument has been inserted through the incision, the surgeon pulls the finger grip 52 of the sheathed cable 50 toward him or to the right as viewed in FIG. 5. This causes the sliders 64, 64' to move downwardly from the FIG. 6 position to the FIG. 7 position, thereby opening the frame members 6, 8 and 10. Frame members 8 and 10 pivot relative to one another at 68. By use of this mechanism, the frame may be opened partially or fully, depending upon the size and shape of the tissue to be compressed or the size of the surgical field. Having thus opened the frames 4 and 32 the desired amount, the surgeon then actuates the scissors 34 to grip and compress the tissue.

I claim:

1. An instrument for use in endoscopic surgery for compressing tissue or organs comprising:
    a straight body member formed along an axis;
    a first frame having a first frame member having one end rigidly attached to the body member and extending along the axis, the opposite end having a pivot;
    a second frame member having one end attached to the pivot on the first frame member and the opposite end having a pivot;
    a third frame member having one end attached to the pivot on the second frame member and the opposite end slidably received by the first frame member for reversible movement along said first frame member;
    the frame members extendable from a compressed or retracted configuration wherein they are parallel to each other and said axis to an extended, polygonal, planar configuration;
    a second frame having frame members corresponding to the frame members of the first frame and extendable in the same manner as the first frame members;
    the second frame in its extended, polygonal, planar configuration being pivoted on the body member for movement relative to the first frame in its extended, polygonal, planar configuration, to and from an open position wherein the frames receive tissue toward a closed position wherein the frames engage and compress tissue.

2. An instrument according to claim 1 wherein there are cable operated means for moving the frame members incrementally between the compressed or retracted configuration and the extended, polygonal, planar configuration.

3. An instrument according to claim 1 wherein there are spring means on each frame for moving its frame members from the compressed or retracted configuration to the extended, polygonal, planar configuration.

4. An instrument for use in endoscopic surgery for compressing tissue or organs comprising:
    a straight body member formed along an axis;
    a first frame having a first frame member having one end rigidly attached to the body member and extending along the axis, the opposite end having a pivot;
    a second frame member having one end attached to the pivot on the first frame member and the opposite end having a pivot;
    a third frame member having one end attached to the pivot on the second frame member and the opposite end slidably received by the first frame member for reversible movement along said first frame member;

the frame members extendable from a compressed or retracted configuration wherein they are parallel to each other and said axis to an extended, polygonal, planar configuration;

a second frame having frame members corresponding to the frame members of the first frame and extendable in the same manner as the first frame members;

the second frame in its extended, polygonal, planar configuration being pivoted on the body member for movement relative to the first frame in its extended, polygonal, planar configuration, to and from an open position wherein the frames receive tissue toward a closed position wherein the frames engage and compress tissue; and manually operated means for moving the frames in their extended, polygonal, planar configurations between the open and closed positions.

5. An instrument according to claim 4 wherein the manually operated means for moving the frames between the open and closed positions is a hinged scissors grip.

6. An instrument according to claim 4 wherein there are cable operated means for moving the frame members incrementally between the compressed or retracted configuration and the extended, polygonal, planar configuration.

7. An instrument according to claim 4 wherein there are spring means on each frame for moving its frame members from the compressed or retracted configuration to the extended, polygonal, planar configuration.

8. An instrument for use in endoscopic surgery for compressing tissue or organs comprising:

a straight body member formed along an axis;

a first frame having a first frame member having one end rigidly attached to the body member and extending along the axis, the opposite end having a pivot;

a second frame member having one end attached to the pivot on the first frame member and the opposite end having a pivot;

a third frame member having one end attached to the pivot on the second frame member and the opposite end slidably received by the first frame member for reversible movement along said first frame member;

the frame members extendable from a compressed or retracted configuration wherein they are parallel to each other and said axis to an extended, polygonal, planar configuration;

a second frame having frame members corresponding to the frame members of the first frame and extendable in the same manner as the first frame members;

the second frame in its extended, polygonal, planar configuration being pivoted on the body member for movement relative to the first frame in its extended, polygonal, planar configuration, to and from an open position wherein the frames receive tissue toward a closed position wherein the frames engage and compress tissue;

manually operated means for moving the frames in their extended, polygonal, planar configurations between the open and closed positions; and tubular means for urging both frames into their compressed or retracted configurations for inserting the instrument into and removing it from an incision in a patient.

9. An instrument according to claim 8 wherein the manually operated means for moving the frames between the open and closed positions is a hinged scissors grip.

10. An instrument according to claim 8 wherein there are cable operated means for moving the frame members incrementally between the compressed or retracted configuration and the extended, polygonal, planar configuration.

11. An instrument according to claim 8 wherein there are spring means on each frame for moving its frame members from the compressed or retracted configuration to the extended, polygonal, planar configuration.

* * * * *